US010092487B2

(12) United States Patent
Gershon et al.

(10) Patent No.: US 10,092,487 B2
(45) Date of Patent: Oct. 9, 2018

(54) PLASMONIC ENHANCEMENT OF ABSORPTION IN SUNSCREEN APPLICATIONS

(71) Applicant: International Business Machines Corporation, Armonk, NY (US)

(72) Inventors: Talia S. Gershon, White Plains, NY (US); Yun Seog Lee, Yorktown Heights, NY (US); Ning Li, White Plains, NY (US); Devendra Sadana, Pleasantville, NY (US); Teodor K. Todorov, Yorktown Heights, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/142,779

(22) Filed: Apr. 29, 2016

(65) Prior Publication Data
US 2017/0112730 A1 Apr. 27, 2017

Related U.S. Application Data

(60) Provisional application No. 62/245,263, filed on Oct. 22, 2015.

(51) Int. Cl.
*A61K 8/11* (2006.01)
*A61Q 17/04* (2006.01)
(Continued)

(52) U.S. Cl.
CPC .......... *A61K 8/11* (2013.01); *A61K 8/19* (2013.01); *A61K 8/25* (2013.01); *A61K 8/27* (2013.01);
(Continued)

(58) Field of Classification Search
None
See application file for complete search history.

(56) References Cited

U.S. PATENT DOCUMENTS 3,761,261 A 9/1973 Ono et al.
3,863,007 A 1/1975 Warner, Jr.
(Continued)

FOREIGN PATENT DOCUMENTS

CN 103071535 A 5/2013
EP 1889810 A1 2/2008
(Continued)

OTHER PUBLICATIONS

Smijs et al. "Titanium dioxide and zinc oxide nanoparticles in sunscreens: focus on their safety and effectiveness," Nanotechnology, Science and Applications 4:95-112, Oct. 2011.*

(Continued)

*Primary Examiner* — Ileana Popa
*Assistant Examiner* — Alissa Prosser
(74) *Attorney, Agent, or Firm* — Ryan, Mason & Lewis, LLP

(57) ABSTRACT

Zinc oxide compositions as well as techniques for plasmonic enhancement of absorption in sunscreen applications are provided herein. A method includes selecting one or more metal particles to be used in conjunction with one or more zinc oxide particles in a sunscreen composition, wherein said selecting is based on the plasmon resonance frequency associated with each of the metal particles; and embedding the one or more selected metal particles into each of the one or more zinc oxide particles.

1 Claim, 2 Drawing Sheets

(51) Int. Cl.
*A61K 8/27* (2006.01)
*A61K 8/25* (2006.01)
*A61K 8/19* (2006.01)

(52) U.S. Cl.
CPC .......... *A61Q 17/04* (2013.01); *A61K 2800/26* (2013.01); *A61K 2800/412* (2013.01); *A61K 2800/413* (2013.01); *A61K 2800/651* (2013.01); *A61K 2800/805* (2013.01)

(56) References Cited

U.S. PATENT DOCUMENTS

| | | | |
|---|---|---|---|
| 4,549,195 | A | 10/1985 | Bluzer |
| 5,011,782 | A | 4/1991 | Lamb |
| 5,030,699 | A | 7/1991 | Hendrickson |
| 5,147,125 | A | 9/1992 | Austin |
| 5,223,250 | A | 6/1993 | Mitchell |
| 5,441,726 | A | 8/1995 | Mitchnick |
| 5,534,056 | A | 7/1996 | Kuehnle |
| 5,553,630 | A | 9/1996 | Dupuis et al. |
| 5,902,569 | A * | 5/1999 | Oshima ............. A61K 8/06 423/462 |
| 6,419,909 | B1 | 7/2002 | Lorant |
| 7,241,399 | B2 | 7/2007 | Haubold |
| 7,514,863 | B2 | 4/2009 | Lee |
| 8,647,373 | B1 | 2/2014 | Shepherd |
| 9,056,063 | B2 | 6/2015 | Hanson |
| 9,144,535 | B1 | 9/2015 | Daly et al. |
| 9,144,536 | B1 | 9/2015 | Daly et al. |
| 9,773,931 | B2 * | 9/2017 | Hossain ............. H01L 31/02366 |
| 2002/0122832 | A1 | 9/2002 | Hanke |
| 2003/0102099 | A1 | 6/2003 | Yadav |
| 2004/0209081 | A1 | 10/2004 | Hagihara |
| 2005/0008861 | A1 | 1/2005 | Yadav et al. |
| 2005/0048010 | A1 | 3/2005 | Kliss |
| 2005/0208005 | A1 | 9/2005 | Giroud |
| 2005/0227063 | A1 * | 10/2005 | Lawandy ............. B82Y 20/00 428/323 |
| 2005/0238600 | A1 | 10/2005 | Lien |
| 2005/0265935 | A1 | 12/2005 | Hollingsworth |
| 2006/0228310 | A1 | 10/2006 | Lyth |
| 2006/0270053 | A1 | 11/2006 | Tilak |
| 2007/0280895 | A1 | 12/2007 | Weimer |
| 2008/0149850 | A1 * | 6/2008 | Tardif ............. B82Y 20/00 250/459.1 |
| 2008/0220026 | A1 | 9/2008 | Maltra et al. |
| 2009/0022765 | A1 | 1/2009 | Chung et al. |
| 2009/0104130 | A1 | 4/2009 | Bernstein |
| 2009/0258072 | A1 | 10/2009 | Schlossman |
| 2009/0258230 | A1 * | 10/2009 | Schlossman ............. A61K 8/19 428/402 |
| 2010/0008872 | A1 | 1/2010 | Katusic |
| 2010/0055138 | A1 | 3/2010 | Margulies |
| 2011/0268678 | A1 | 11/2011 | Armstrong |
| 2013/0216834 | A1 | 8/2013 | Hashimoto |
| 2014/0142213 | A1 * | 5/2014 | Weiss ............. A01N 59/16 523/122 |
| 2015/0283059 | A1 | 10/2015 | Nagare |
| 2016/0082513 | A1 | 3/2016 | Niedermeyer |

FOREIGN PATENT DOCUMENTS

| | | | |
|---|---|---|---|
| JP | 09059591 A | 3/1997 | |
| JP | 2008024677 A | 2/2008 | |
| JP | 2008024677 A * | 2/2008 | |
| JP | 2011102291 A | 5/2011 | |
| WO | WO 2005023535 A2 * | 3/2005 | ........... A61K 8/0237 |
| WO | WO 2008017176 A2 * | 2/2008 | ........... A01N 59/16 |
| WO | 2008079758 A1 | 7/2008 | |
| WO | 2011004133 A2 | 1/2011 | |
| WO | WO 2011004133 A2 * | 1/2011 | ........... A61K 8/0283 |
| WO | 2011089571 A2 | 7/2011 | |
| WO | 2012046204 A1 | 4/2012 | |
| WO | WO 2012046204 A1 * | 4/2012 | ........... A61K 8/025 |
| WO | 2013040149 | 3/2013 | |
| WO | 2013094639 A1 | 6/2013 | |
| WO | 2014040177 A1 | 3/2014 | |
| WO | 2014049139 A1 | 4/2014 | |
| WO | 2014077189 | 5/2014 | |
| WO | 2016020168 A1 | 2/2016 | |

OTHER PUBLICATIONS

Wikipedia "List of refractive indices," last modified Feb. 15, 2017; https://en.wikipedia.org/wiki/List_of_refractive_indices.*
Machine translation WO 2011/004133, printed 2017.*
Machine translation JP 2008-024677, printed 2018.*
Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.
Sardar et al., Optical-absorption intensities and intermanifold emission cross sections of trivalent erbium ions in calcium fluorophosphate, Journal of Applied Physics, Sep. 2005.
Lu et al., 2008—White Up-Conversion Luminescence in Rare-Earth-Ion-Doped YAlO3 Nanocrystals, J. Phys. Chem. C 2008, 112, 15071-15074.
Refractive index of ZnO (Zinc oxide)—Bond-o, http://refractiveindex.info/?shelf=main&book=ZnO&page=Bond-o, Mar. 25, 2016.
Refractive index of SiO2 (Silicon dioxide, Silica, Quartz)—Malitson, http://refractiveindex.info/?shelf=main&book=SiO2&page=Malitson, Mar. 25, 2016.
Schubert et al., Design of multilayer antireflection coatings made from co-sputtered and low-refractive-index materials by genetic algorithm. Optics Express vol. 16, No. 8, 2008.
Law et al., ZnO—Al2O3 and ZnO—TiO2 Core-Shell Nanowire Dye-Sensitized Solar Cells. J. Phys. Chem. B 2006, 110, 22652-22663.
Pu et al., Core/shell structured ZnO/SiO2 nanoparticles: Preparation, characterization and photocatalytic property. Applied Surface Science 257 (2010) 393-397.
Mantz et al., Progress in Organic Coatings 47 (2003) 432-442, "A multiple-scattering model analysis of zinc oxide pigment for spacecraft thermal control coatings.".
Song et al., Toxicology Letters 199 (2010) 389-397, "Role of the dissolved zinc io and reactive oxygen species in cytotoxicity of ZnO nanoparticles."
Bae et al., J. Phys. Chem. B 2005, 109, 2526-2531, "Comparative Structure and Optical Properties of Ga-, In-, and Sn-Doped ZnO Nanowires Synthesized by thermal evaporation."
NanoComposix, Silver Nanoparticles: Optical Properties, http://nanocomposix.com/pages/silver-nanoparticles-optical-properties, Apr. 20, 2016.
Awazu et al., 2007—A Plasmonic Photocatalyst Consisting of Silver Nanoparticles Embedded in Titanium Dioxide, J. AM. CHEM. SOC. 2008, 130, 1676-1680.
Sherry et al., Localized Surface Plasmon Resonance Spectroscopy of Single Silver Nanocubes, Nano Lett., vol. 5, No. 10, 2005.
Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.
Haynes et al., Nanosphere Lithography: Tunable Localized Surface Plasmon Resonance Spectra of Silver Nanoparticles, J. Phys. Chem. B 2000, 104, 10549-10556.
U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.
Tsuzuki et al., Nanoparticle Coatings for UV Protective Textiles, RJTA vol. 14 No. 2 2010.
Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

(56) References Cited

OTHER PUBLICATIONS

Li et al., 2011—Sol-gel preparation and characterization of nanoporous ZnO_SiO2 coatings with broadband antireflection properties, Applied Surface Science 257 (2011) 9752-9756.
Messaoudi et al., "Synthesis and characterization of ZnO/Cu2O core-shell nanowires grown by two-step electrodeposition method." Applied Surface Science 343 (2015) 148-152.
Luo et al., Facile synthesis of composition-tuned ZnO/ZnxCd1-xSe nanowires for photovoltaic applications, Nanoscale Research Letters (2015) 10:181.
List of IBM Patents or Applications Treated as Related, 2016.
Naylor et al. "Sunscreens," accessed 2017, http://telemedicine.org/sundam/sundam2.4.2.html.
Bohren et al., "Absorption and Scattering of Light by Small Particles," Table of Contents, Wiley-VCH, © 2004, Weinheim.
Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.
Ultraviolet Radiation and the INTERSUN Programme [online]. WHO, Nov. 2003 [retrieved on Jun. 8, 2017]. Retrieved from the internet <http://www.who.int/uv/uv_and_health/en/>.
Cuprous Oxide, Chemical Book, pp. 1-4, Accessed Sep. 18, 2017, https://www.chemicalbook.com/ProductChemicalPropertiesCB9853041_EN.htm.
Tariq Jan, et al. Sn Doping Induced Enhancement in the Activity of ZnO Nanostructures Against Antibiotic Resistant S. aureus Bacteria; Int J. Nanomedicine, vol. 8, pp. 3679-3687; Published online Sep. 30, 2013.
Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.
Wikipedia "Band Gap" last modified Jul. 18, 2017, https://en.wikipedia.org/wiki/Band_gap.
Machine translation WO 2012/046204, printed 2017.
Family Health Team, "Best Ways to Protect Your Hair From Sun Damage," Cleveland Clinic, health essentials, (https://health.clevelandclinic.org/2014/06/best-ways-to-protect-your-hair-from-sun-damage/>, published Aug. 22, 2014, p. 1-4.
Machine translation, JP 2008-024677, printer 2018.
Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.
Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).
English language translation of WO 2013 094639 (A1) (Year: 2013).
Latha et al. "Sunscreening Agents: A Review," Journal of Clinical and Aesthetic Dermatology 6(1):16-26, 2013.
Sreejith et al. "Squaraine Dyes: A Mine of Molecular Materials," Journal of Materials Chemistry 18:264-274, 2008.

\* cited by examiner

US 10,092,487 B2

PLASMONIC ENHANCEMENT OF ABSORPTION IN SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, zinc oxide compositions, methods of fabrications thereof and methods of use thereof are provided. An exemplary method can include selecting one or more metal particles to be used in conjunction with one or more zinc oxide particles in a sunscreen composition, wherein said selecting is based on the plasmon resonance frequency associated with each of the metal particles. The method can also include embedding the one or more selected metal particles into each of the one or more zinc oxide particles.

In another embodiment of the invention, a sunscreen composition can include multiple zinc oxide particles suspended within a medium, and one or more metal particles embedded into each of the multiple zinc oxide particles, wherein each of the metal particles comprises a plasmon resonance frequency that supplements the light absorption capabilities of the multiple zinc oxide particles.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes ZnO compositions as well as techniques for plasmonic enhancement of absorption in sunscreen applications. As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm). As used herein, "scattering" refers to the deflection of rays of visible light from the rays' original path due to interaction with particle surfaces.

At least one embodiment of the invention includes enhancing light absorption capabilities of ZnO particles by using plasmonic resonances. As detailed herein and illustrated via the example embodiments depicted in FIGS. 1-3, one or more embodiments of the invention can include generating a structure that is designed to utilize the plasmonic enhancement of light intensity near a metal particle surface. In such an embodiment, one or more metal particles are enclosed and/or embedded inside a ZnO particle to generate plasmonic enhancement of absorption in the resulting composition.

Figure 1:
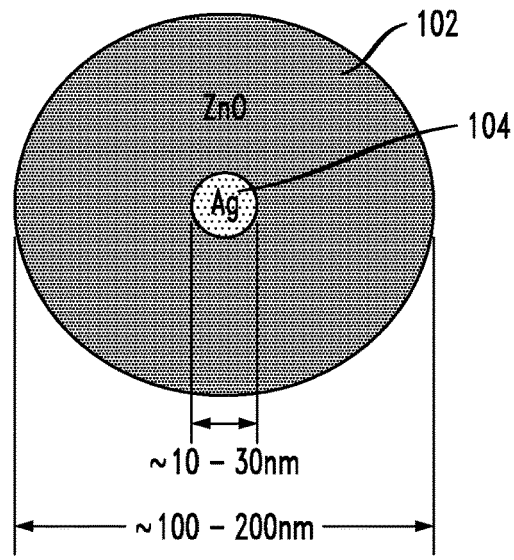
FIG. 1 is a diagram illustrating a metal particle embedded within a ZnO particle, according to an example embodiment of the invention.

FIG. 1 is a diagram illustrating a metal particle 104 embedded within a ZnO particle 102, according to an example embodiment of the invention. In one or more embodiments of the invention, the metallic and/or plasmonic particle 104 can include a silver (Ag) particle or a gold (Au) particle. Also, in at least one embodiment of the invention, the metallic and/or plasmonic particle 104 can be less than 30 nm in diameter (for example, between 10 and 30 nm in diameter). Additionally, the ZnO particle 102 can be approximately 200 nm in diameter (for example, between 100 and 200 nm in diameter) to utilize the plasmonic effect of the metal particle 104 and maximize the plasmonic enhancement absorption of the resultant composition. In accordance with one or more embodiments of the invention, the electric field is only enhanced within approximately 100 nm of the metallic particle 104.

Figure 2:
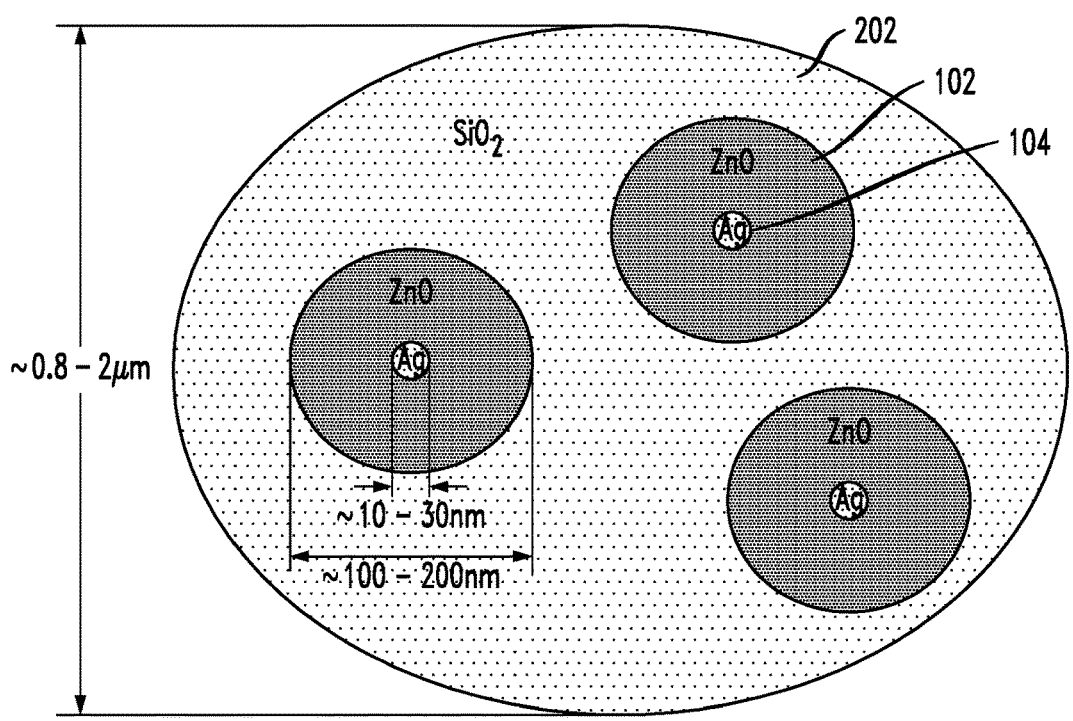
FIG. 2 is a diagram illustrating ZnO particles, each embedded with a metal particle, embedded within a silicon dioxide ($SiO_2$) particle, according to an example embodiment of the invention.

FIG. 2 is a diagram illustrating ZnO particles 102, each embedded with a metal particle 104, embedded within a $SiO_2$ particle 202, according to an example embodiment of the invention. While the example embodiment depicted in FIG. 2 utilizes a $SiO_2$ particle 202, it is to be appreciated that one or more embodiments of the invention can utilize any material that has a large band gap (greater than approximately ~3.2 electron volts (eV), for example) and a refractive index in between that of ZnO and air. Additionally, the $SiO_2$ particle 202, as depicted in the FIG. 2 example, can be (approximately) between 0.8-2.0 micrometers in diameter.

Figure 3:
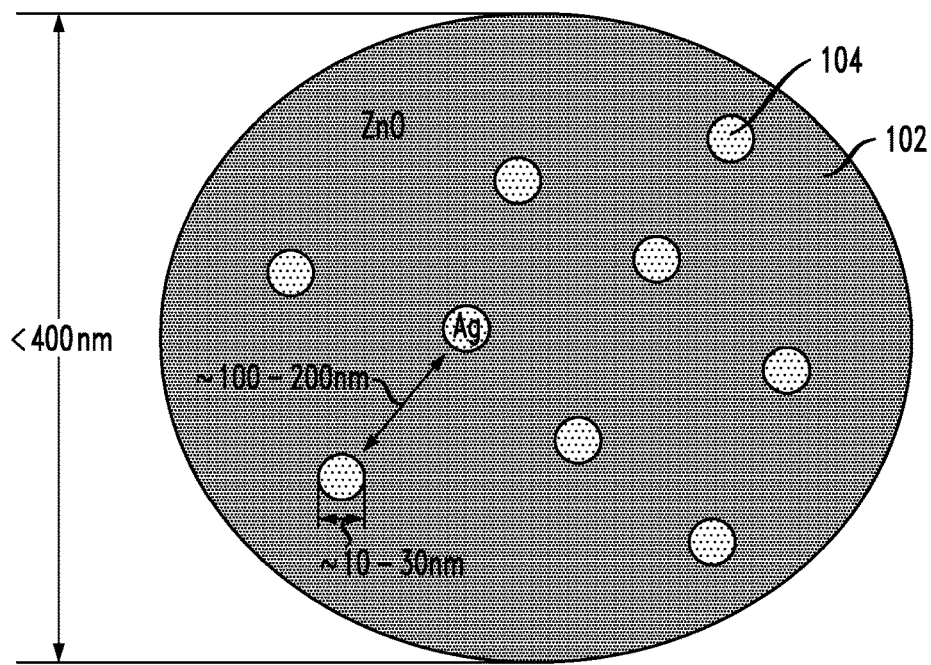
FIG. 3 is a diagram illustrating multiple metal particles embedded within a ZnO particle.

FIG. 3 is a diagram illustrating multiple metal particles 104 embedded within a ZnO particle 102. In one or more embodiments of the invention, the distance between metal particles 104 can include any distance amount so as to ensure that the metal particles 104 are physically separate from one another. In one example, such as depicted in FIG. 3, the distance between the metal particles 104 can be approximately 100-200 nm. Also, in one or more embodiments of the invention (such as the example embodiment depicted in FIG. 3), the size of each individual ZnO particle 102 can be reduced (for use in a sunscreen composition) to less than 400 nm. By way of example, at least one embodiment of the invention includes reducing the size of each ZnO particle to a size of between approximately 100 and 400 nm.

Further, it is noted that the example ZnO particle depicted in FIG. 3 (embedded with multiple metal particles) can also be utilized as illustrated in FIG. 2; that is, the example ZnO particle depicted in FIG. 3 (embedded with multiple metal particles) can be embedded within a $SiO_2$ particle 202, in accordance with one or more embodiments of the invention.

Figure 4:
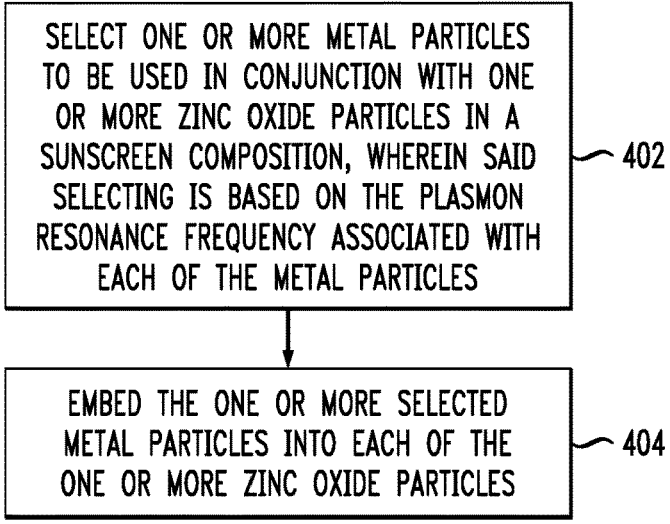
FIG. 4 is a flow diagram illustrating techniques, according to an embodiment of the invention.

FIG. 4 is a flow diagram illustrating techniques, according to an embodiment of the present invention. Step 402 includes selecting one or more metal particles to be used in conjunction with one or more zinc oxide particles in a sunscreen composition, wherein said selecting is based on the plasmon resonance frequency associated with each of the metal particles. Step 404 includes embedding the one or more selected metal particles into each of the one or more zinc oxide particles.

In at least one embodiment of the invention, each of the zinc oxide particles can include a size of less than 400 nanometers in diameter, and each of the one or more metal particles can include a size of less than 30 nanometers. Additionally, the one or more metal particles can include one or more silver particles and/or one or more gold particles. Further, in one or more embodiments of the invention, the one or more metal particles can include multiple metal particles, wherein the multiple metal particles are each physically separated within each of the one or more zinc oxide particles.

The techniques depicted in FIG. 4 can also include selecting one or more suspension particles to be utilized in conjunction with the multiple zinc oxide particles, wherein each of the one or more suspension particles is larger in size than each of the multiple zinc oxide particles, and wherein said selecting is based on the refractive index of each of the one or more suspension particles. One or more embodiments of the invention can also include embedding the multiple zinc oxide particles into the one or more suspension particles. Additionally, in such an embodiment, the one or more suspension particles can include one or more silicon dioxide particles, and each of the one or more suspension particles can include a size of between 0.8 and 2 micrometers. Further, in at least one embodiment of the invention, the refractive index of each of the one or more suspension particles is between that of air and zinc oxide.

Also, an additional embodiment of the invention includes a sunscreen composition that includes multiple zinc oxide particles suspended within a medium, and one or more metal particles embedded into each of the multiple zinc oxide particles, wherein each of the metal particles comprises a plasmon resonance frequency that supplements the light absorption capabilities of the multiple zinc oxide particles. Such a composition can also include one or more suspension particles, wherein each of the one or more suspension particles is larger in size than each of the multiple zinc oxide particles, and wherein each of the multiple zinc oxide particles is embedded into the one or more suspension particles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, generating a structure that is designed to utilize the plasmonic enhancement of light intensity near a metal particle surface.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A sunscreen composition comprising:
   multiple zinc oxide particles suspended within a silicon dioxide particle, wherein each of the zinc oxide particles is between approximately 100 nanometers and approximately 400 nanometers in diameter, and wherein the silicon dioxide particle is between approximately 0.8 micrometers and approximately 2 micrometers in diameter; and
   nine silver particles embedded into each of the multiple zinc oxide particles, wherein each of the nine silver particles is between approximately 10 nanometers and approximately 30 nanometers in diameter, and wherein the nine silver particles are physically separated within each of the zinc oxide particles by a distance of between approximately 100 nanometers and approximately 200 nanometers between each of the silver particles.

\* \* \* \* \*